United States Patent [19]

Andrews

[11] 4,393,180
[45] Jul. 12, 1983

[54] CURING AGENTS FOR EPOXIDE RESINS AND COMPOSITIONS CONTAINING THEM

[75] Inventor: Christopher M. Andrews, Cambridge, England

[73] Assignee: Ciba-Geigy Corporation, Ardsley, N.Y.

[21] Appl. No.: 390,468

[22] Filed: Jun. 21, 1982

[30] Foreign Application Priority Data

Jun. 30, 1981 [GB] United Kingdom ................ 8120142

[51] Int. Cl.³ ...................... C08L 61/00; C08L 61/06
[52] U.S. Cl. ................................... 525/504; 528/12; 528/20; 528/27; 528/88; 528/123
[58] Field of Search ................... 528/12, 20, 27, 88, 528/123; 525/504, 507

[56] References Cited

U.S. PATENT DOCUMENTS

| | | | |
|---|---|---|---|
| 3,072,594 | 1/1963 | Shultz et al. | 260/43 |
| 3,297,608 | 1/1967 | Noshay et al. | 528/123 X |
| 3,455,725 | 7/1969 | Jex et al. | 525/504 X |
| 3,505,381 | 4/1970 | Kotzsch et al. | 260/448.8 |
| 3,847,860 | 11/1974 | Seiler et al. | 525/504 X |
| 3,979,362 | 9/1976 | Blount | 528/12 X |

FOREIGN PATENT DOCUMENTS 867487 5/1961 United Kingdom .

OTHER PUBLICATIONS

Derwent C.P.I. Abstract No. 89720B/50.

Primary Examiner—Lucille M. Phynes
Attorney, Agent, or Firm—Harry Falber

[57] ABSTRACT

Curable compositions contain an epoxide resin and, as curing agent, a mixture of
(a) a silamine of the general formula

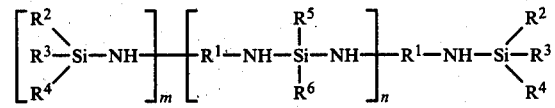

wherein
either m represents 1, in which case $R^1$ represents the divalent residue of an aromatic, aliphatic, araliphatic, or cycloaliphatic diprimary amine after removal of two primary amino groups, and n represents zero or an integer of from 1 to 10, or m represents 2, in which case $R^1$ represents the trivalent residue of an aliphatic triprimary amine after removal of the three primary amino groups, and n represents zero, and
$R^2$, $R^3$, $R^4$, $R^5$, and $R^6$, which may be the same or different, represent alkyl or aryl groups, and
(b) a substantially anhydrous organic acid or a phenol.

These compositions are stable for prolonged periods in the absence of water, but cure rapidly at room temperature or at elevated temperatures in the presence of water, which may be as water vapor or liquid water.

10 Claims, No Drawings

CURING AGENTS FOR EPOXIDE RESINS AND COMPOSITIONS CONTAINING THEM

BACKGROUND OF THE INVENTION

This invention relates to compositions for curing epoxide resins, to curable mixtures of these compositions and epoxide resins, and to cured products obtained by curing the aforesaid mixtures.

It is known that epoxide resins, i.e., substances containing on average more than one 1,2-epoxide group per molecule, may be cured by reaction with various classes of substances to form cross-linked, infusible, insoluble products having valuable technical properties. Typical curing agents include polyamines.

These are useful curing agents, and may be employed to cure epoxide resins at room temperature or at elevated temperatures. They suffer from the drawback, however, that curing commences as soon as they are mixed with the epoxide resin and so it is not possible to make 'one shot' mixtures, i.e., mixtures of epoxide resins and such hardeners which remain stable on storage until required for use.

British Patent Specification No. 867,487 describes compounds prepared by the reaction of at least one epoxide group and a silicon-nitrogen compound (a 'silamine'), itself prepared by reaction of a halosilane with ammonia or a primary amine. Suitable halosilanes used in the reaction are of the generic formula $$R_p\text{—Si—Hal}_{4-p} \qquad \text{I}$$

where R represents a hydrogen atom or an organic group, and p is 1, 2, or 3. Suitable amines include methylamine, ethylamine, allylamine, ethylenediamine, hexamethylenediamine, aniline, p-phenylenediamine, and benzylamine. It is stated that silamines will cure epoxide resins at room temperature and that silamines made from primary amines tend to react with epoxy resins somewhat more rapidly than silamines derived from ammonia. The combination of epoxy resin and silamine has an exceedingly short 'shelf-life' it is said, and the components are mixed only immediately before use. However, it is further stated that certain of the silamines may be used as curing agents for epoxide resins wherein the mixture of curing agent and resin has a shelf-life of days or weeks. From what is stated previously it is implied that these less-active silamines are those derived from ammonia.

That specification gives no example of a silamine prepared from a monohalosilane and no example of a silamine prepared from a diamine although such are included within the general description. Further, that specification indicates that no mixture of an epoxide and a silamine would be stable for longer than a few weeks.

We have now found that combinations of epoxide resins with silamines derived from a monohalosilane and a di- or polyamine, the said combinations further containing a substantially anhydrous organic acid or phenol, are stable in the absence of moisture for several months at room temperatures and at elevated temperatures up to about 80° C. Such combinations will then cure rapidly at room temperature or elevated temperature when exposed to water or water vapour. These combinations therefore form a storage-stable but rapidly-curing 'one-shot' epoxide resin composition.

SUMMARY OF THE INVENTION

One aspect of this invention comprises compositions, suitable as curing agents for epoxide resins, containing
(a) a silamine of the formula

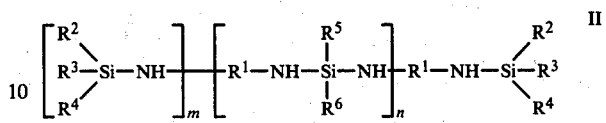

where
either m represents 1, in which case $R^1$ represents the divalent residue of an aromatic, aliphatic, araliphatic, or cycloaliphatic diprimary amine after removal of the two primary amino groups and n represents zero or an integer of from 1 to 10, or m represents 2, in which case $R^1$ represents the trivalent residue of an aliphatic triprimary amine after removal of the three primary amino groups and n represents zero, and $R^2$, $R^3$, $R^4$, $R^5$, and $R^6$, which may be the same or different, each represent an alkyl or aryl group, and (b) a substantially anhydrous organic acid or a substantially anhydrous phenol.

DESCRIPTION OF THE PREFERRED EMBODIMENTS

Suitable groups $R^1$ have from 2 to 20 carbon atoms and include ethylene, hexamethylene, trimethylhexamethylene such as 2,2,4-trimethylhexamethylene and 2,3,3-trimethylhexamethylene, xylylene such as m-xylylene, cyclohexylene, substituted cyclohexylene, such as the substituted cyclohexylenemethylene group of formula

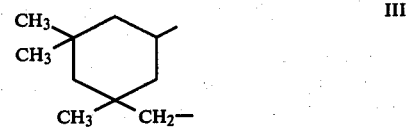

and also bis(phenylene)methane such as bis(p-phenylene)methane, bis(phenylene) sulphone such as bis(p-phenylene) sulphone, 2,2-bis(phenylene)propane such as 2,2-bis(p-phenylene)propane, and phenylene such as 1,3-phenylene.

Suitable groups $R^2$, $R^3$, $R^4$, $R^5$, and $R^6$ include alkyl groups of 1 to 8 carbon atoms, such as methyl, ethyl, and n-propyl groups, and aryl groups of 6 to 10 carbon atoms, such as phenyl groups, optionally substituted by one or more alkyl groups of 1 to 4 carbon atoms or by one or more halogen atoms. In the particularly preferred compounds of formula II, m represents 1, n represents zero or 1, and $R^2$ to $R^6$ each denote a methyl group.

Another aspect of this invention comprises curable compositions containing
(a) a silamine of formula II,
(b) a substantially anhydrous organic acid or a substantially anhydrous phenol, and
(c) an epoxide resin.

Further aspects of this invention provide a process for curing an epoxide resin which comprises forming a mixture of the epoxide resin, a silamine of formula II, and a substantially anhydrous organic acid or a substantially anhydrous phenol, and exposing the mixture to water or water vapour at ambient or elevated temperature, and cured products made by this process.

Silamines of formula II may be prepared by reaction of a primary di- or tri-amine of formula $$H_2N-R^1-(NH_2)_m \qquad IV$$

where $R^1$ and m are as hereinbefore defined, with a monohalosilane of formula $$\begin{array}{c} R^2 \\ R^3-Si-X \\ R^4 \end{array} \qquad V$$

and optionally, when m in the amine of formula IV represents 1, also with a dihalosilane of formula $$\begin{array}{c} R^5 \\ | \\ X-Si-X \\ | \\ R^6 \end{array} \qquad VI$$

where
$R^1$, $R^2$, $R^3$, $R^4$, $R^5$, and $R^6$ are as hereinbefore defined and
X represents a halogen, preferably a chlorine, atom.

The silamines of formula II are prepared from an amine (IV), a monohalosilane (V) and a dihalosilane (VI) in the molar ratio n+1:2:n, where n is as hereinbefore defined. This reaction is effected under anhydrous conditions by heating the reactants, usually at 50° to 150° C., for a period of from 30 minutes to 5 hours, especially for 1-2 hours, in an inert solvent such as an aromatic hydrocarbon, an ether, a halogenated hydrocarbon, or a ketone, and in the presence of an acid acceptor such as a tertiary amine, especially pyridine or triethylamine.

Suitable diprimary amines of formula IV which may be used in the preparation of the silamines of formula II include m-phenylenediamine, bis(p-aminophenyl)methane, bis(p-aminophenyl) sulphone, 5-amino-1,3,3-trimethylcyclohexylmethylamine ("isophoronediamine"), and m-xylylenediamine. Suitable triprimary amines of formula IV include polyoxypropylene triamines.

Preferred monohalosilanes of formula V include trimethylchlorosilane, triethylchlorosilane, tripropylchlorosilane, triphenylchlorosilane, trimethylbromosilane, and trimethyliodosilane. Trimethylchlorosilane is particularly preferred. A preferred dihalosilane of formula VI is dimethyldichlorosilane.

The acids used in the present compositions may be mono-, di-, or poly-basic. As stated previously, they must be substantially anhydrous, by which is meant that they must contain insufficient water to cause hydrolysis of the silamines of formula II at ambient temperature. Suitable such acids include acetic, phthalic, methanesulphonic, salicylic, maleic, 2,2-dichloropropionic, adipic, trimellitic, and cyanoacetic acids and, where they are di- or poly-basic, their partial esters (such as 2-methoxyethyl hydrogen maleate).

Phenols which may be used in the present compositions must likewise be substantially anhydrous. They may be mono-, di-, or polyhydric and include phenol itself, alkylated phenols such as 2,6-di-tert.butyl-4-methylphenol (which is preferred), halogenated phenols, resorcinol, bisphenol F, and hisphenol A.

The weight ratio of acid or phenol to epoxide resin in the present compositions is usually within the range 0.5-20:100, and especially 2-15:100.

Epoxide resins which may be employed in these compositions as component (c) should be, as should other components to be incorporated, substantially anhydrous (unless it is required to initiate cure). Preferably the epoxide resins are those containing groups of formula $$\begin{array}{c} O \\ / \quad \backslash \\ -CH-C-\!\!\!-\!\!\!-CH \\ | \quad | \quad | \\ R^7 \quad R^8 \quad R^9 \end{array} \qquad VII$$

directly attached to atoms of oxygen, nitrogen, or sulphur, where either $R^7$ and $R^9$ each represent a hydrogen atom, in which case $R^8$ denotes a hydrogen atom or a methyl group, or $R^7$ and $R^9$ together represent $-CH_2CH_2-$, in which case $R^8$ denotes a hydrogen atom.

As examples of such resins may be mentioned polyglycidyl and poly(β-methylglycidyl) esters obtainable by reaction of a compound containing two or more carboxylic acid groups per molecule with epichlorohydrin, glycerol dichlorohydrin, or β-methylepichlorohydrin in the presence of an alkali. Such polyglycidyl esters may be derived from aliphatic polycarboxylic acids, e.g., oxalic acid, succinic acid, glutaric acid, adipic acid, pimelic acid, suberic acid, azelaic acid, sebacic acid, or dimerised or trimerised linoleic acid; from cycloaliphatic polycarboxylic acids such as tetrahydrophthalic acid, 4-methyltetrahydrophthalic acid, hexahydrophthalic acid, and 4-methylhexahydrophthalic acid; and from aromatic polycarboxylic acids such as phthalic acid, isophthalic acid, and terephthalic acid.

Further examples are polyglycidyl and poly(β-methylglycidyl) ethers obtainable by reaction of a compound containing at least two free alcoholic hydroxyl and/or phenolic hydroxyl groups per molecule with the appropriate epichlorohydrin under alkaline conditions or, alternatively, in the presence of an acidic catalyst and subsequent treatment with alkali. These ethers may be made from acyclic alcohols such as ethylene glycol, diethylene glycol, and higher poly(oxyethylene) glycols, propane-1,2-diol and poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, pentaerythritol, sorbitol, and poly(epichlorohydrin); from cycloaliphatic alcohols such as resorcitol, quinitol, bis(4-hydroxycyclohexyl)-methane, 2,2-bis(4-hydroxycyclohexyl)propane, and 1,1-bis(hydroxymethyl)cyclohex-3-ene; and from alcohols having aromatic nuclei, such as N,N-bis(2-hydroxyethyl)aniline and p,p'-bis(2-hydroxyethylamino)diphenylmethane. Or they may be made from mononuclear phenols, such as resorcinol and hydroquinone, and from polynuclear phenols, such as bis(4-hydroxyphenyl)methane, 4,4'-dihydroxydiphenyl, bis(4-hydroxyphenyl) sulphone, 1,1,2,2-tetrakis(4-hydroxyphenyl)-ethane, 2,2-bis(4-hydroxyphenyl)propane, 2,2-bis(3,5-dibromo-4-hydroxyphenyl)propane, and novolaks formed from aldehydes such as formaldehyde, acetaldehyde, chloral, and furfuraldehyde, with phenols such as phenol itself, and phenol substituted in the ring by chlorine atoms or by alkyl groups each containing up to nine carbon atoms, such as 4-chlorophenol, 2-methylphenol, and 4-tert.butylphenol.

Poly(N-glycidyl) compounds include, for example, those obtained by dehydrochlorination of the reaction products of epichlorohydrin with amines containing at least two amino-hydrogen atoms, such as aniline, n-butylamine, bis(4-aminophenyl)methane, and bis(4-methylaminophenyl)methane; triglycidyl isocyanurate; and N,N'-diglycidyl derivatives of cyclic alkylene ureas, such as ethyleneurea and 1,3-propyleneurea, and of hydantoins such as 5,5-dimethylhydantoin.

Examples of poly(S-glycidyl) compounds are di-S-glycidyl derivatives of dithiols such as ethane-1,2-dithiol and bis(4-mercaptomethylphenyl) ether.

Examples of epoxide resins having groups of formula VII where $R^7$ and $R^9$ conjointly denote a —CH$_2$CH$_2$— group are bis(2,3-epoxycyclopentyl) ether, 2,3-epoxycyclopentyl glycidyl ether, and 1,2-bis(2,3-epoxycyclopentyloxy)ethane.

Epoxide resins having the 1,2-epoxide groups attached to different kinds of hetero atoms may be employed, e.g., the N,N,O-triglycidyl derivative of 4-aminophenol, the glycidyl ether-glycidyl ester of salicylic acid, N-glycidyl-N'-(2-glycidyloxypropyl)-5,5-dimethylhydantoin, and 2-glycidyloxy-1,3-bis(5,5-dimethyl-1-glycidylhydantoin-3-yl)propane.

If desired, a mixture of epoxide resins may be used.

Preferred epoxide resins are polyglycidyl ethers, polyglycidyl esters, and N,N'-diglycidylhydantoins. Specific preferred resins are polyglycidyl ethers of 2,2-bis(4-hydroxyphenyl)propane, of bis(4-hydroxyphenyl)methane, or of a novolak formed from formaldehyde and phenol, or phenol substituted in the ring by one chlorine atom or by one alkyl hydrocarbon group containing from one to nine carbon atoms, and having a 1,2-epoxide content of more than 0.5 equivalent per kilogram.

An effective, i.e. a curing, amount of the silamine must be used. Normally there will be used from about 0.7 to about 1.4 theoretical amino-hydrogen equivalents of the silamine of formula II per 1,2-epoxide equivalent of the epoxide resin. By the term "theoretical amino-hydrogen equivalents", as used in the present specification and claims, is meant the number of amino-hydrogen equivalents present after removal of substantially all the silyl groups by hydrolysis, each molecule of the silamine affording (2(l+m+2n) such equivalents.

Curing can be carried out, depending on the desired rate of cure, at room temperature (18° to 25° C., for example) or at higher temperatures, up to about 100° C. Room temperature cure is, however, preferred.

Water required to initiate the curing reaction may be obtained in a variety of ways. It may, for example, be atmospheric moisture, or the resin-silamine mixture may be placed in contact with liquid water, either directly or through a semi-permeable membrane. Alternatively, the composition may be contacted with a material that contains water, such as wood or a porous material such as concrete or brickwork.

The new compositions may further contain suitable plasticisers such as dibutyl phthalate and dioctyl phthalate, inert diluents such as tars and bitumen and so-called reactive diluents, especially monoepoxides such as n-butyl glycidyl ether, iso-octyl glycidyl ether, phenyl glycidyl ether, cresyl glycidyl ethers, glycidyl esters of tertiary, aliphatic, monocarboxylic acids, glycidyl acrylate, and glycidyl methacrylate. They may also contain additives such as fillers, reinforcing materials, colouring matter, flow control agents, flame inhibitors, and mould lubricants. Suitable extenders, fillers, and reinforcing materials are, for example, glass fibres, carbon fibres, ballotini, mica, quartz flour, calcium carbonate, cellulose, kaolin, wollastonite, colloidal silica having a large specific surface area, powdered poly(vinyl chloride), and powdered polyolefin hydrocarbons such as polyethylene and polypropylene.

The curable compositions of this invention may be used as laminating resins, paints and lacquers, impregnating and casting resins, moulding compositions, putties and sealing compounds, potting and insulating compounds for the electrical industry, and adhesives, and also in the manufacture of such products.

The following Examples illustrate the invention.

Silamines used in these Examples were prepared as follows:

Silamine I

Bis(4-aminophenyl)methane (20 g; 0.1 mole) was mixed with triethylamine (20.2 g; 0.2 mole) in dry toluene (100 ml). Trimethylchlorosilane (21.7 g; 0.2 mole) was added dropwise to the stirred mixture over 1 hour, and stirring was continued at room temperature for a further 5 hours. Next, the mixture was heated under reflux for 1 hour. The mixture was cooled, filtered to remove triethylamine hydrochloride, and the toluene was distilled off in vacuo from a water bath at 80° C. The residue, bis(4-(trimethylsilylamino)phenyl)methane, weighed 32.5 g, and is hereinafter referred to as 'Silamine I'. This product has a theoretical amino-hydrogen equivalent weight of 85.5, i.e., its theoretical amino-hydrogen content is 11.69 equivalents/kg.

Silamine II m-Phenylenediamine (10.8 g; 0.1 mole) and triethylamine (20.2 g; 0.2 mole) in dry toluene (100 ml) were stirred and treated with trimethylchlorosilane (21.7 g; 0.2 mole) which was added dropwise over 1 hour. Stirring was continued for a further hour, and the mixture was then heated under reflux for 1 hour. After cooling and filtering the product, the solvent was evaporated to leave 24.2 g of m-bis(trimethylsilylamino)benzene, which is hereinafter referred to as Silamine II. This product has a theoretical amino-hydrogen equivalent weight of 63, i.e., its theoretical amino-hydrogen content is 15.87 equivalents/kg.

Silamine III

Bis(4-aminophenyl)methane (40 g; 0.2 mole) and triethylamine (40.4 g; 0.4 mole) in dry toluene (200 ml) were stirred and treated with a mixture of trimethylchlorosilane (21.7 g; 0.2 mole) and dimethyldichlorosilane (12.9 g; 0.1 mole) which was added dropwise over 1 hour. Stirring was continued for a further hour and the mixture was then heated under reflux for 2 hours, filtered, and the solvent was distilled off to leave 54 g of 'Silamine III' which is a mixture having an average structure of formula II in which $R^1$ is of formula

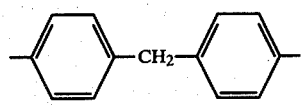

VIII $R^2$, $R^3$, $R^4$, $R^5$ and $R^6$ all denote methyl groups, and m and n denote 1. This product has a theoretical amino-hydrogen equivalent weight of 74, i.e., its theoretical amino-hydrogen content is 13.5 equivalents/kg. It has the average structure dimethylbis(p-(p'-(trimethyl-silylamino)benzyl)phenylamino)silane.

Silamine IV

Isophoronediamine (17.0 g; 0.1 mole) and triethylamine (20.2 g; 0.2 mole) were stirred in dry toluene (100 ml) and treated over 1 hour with trimethylchlorosilane (21.7 g; 0.2 mole). After stirring the mixture for a further 10 hours it was heated under reflux for 1 hour, cooled, and filtered. The filtrate was evaporated to give 29.8 g of 'Silamine IV' which is of formula II in which $R^1$ is of formula III, $R^2$, $R^3$, $R^4$ all denote methyl groups, m is 1, n is zero, i.e., 1,1,3-trimethyl-3-(trimethylsilylaminomethyl)-5-(trimethylsilylamino)cyclohexane. This product has a theoretical amino-hydrogen equivalent weight of 78.5, i.e., its theoretical amino-hydrogen content is 11.4 equivalents/kg.

Silamine V m-Xylylenediamine (12.6 g; 0.1 mole) and triethylamine (20.2 g; 0.2 mole) were stirred in dry toluene (100 ml) and treated over 1 hour with trimethylchlorosilane (21.7 g; 0.2 mole). After the mixture had been stirred for a further 10 hours it was heated under reflux for 1 hour, cooled, and filtered. The filtrate was evaporated to give 25.2 g of 'Silamine V'. This product, 1,3-bis(trimethylsilylaminomethyl)benzene, has a theoretical amino-hydrogen equivalent weight of 70, i.e., its theoretical aminohydrogen content is 14.29 equivalents/kg.

Silamine VI

This was made as described for Silamine I except that instead of bis(4-aminophenyl)methane there was used a corresponding amount of a commercially available mixture of 2,2,4-trimethylhexane-1,6-diamine and 2,3,3-trimethylhexane-1,6-diamine. The product, a mixture of 1,6-bis(trimethylsilylamino)-2,2,4-trimethylhexane and 1,6-bis(trimethylsilylamino)-2,3,3-trimethylhexane, has a theoretical amino-hydrogen equivalent weight of 76, i.e., its theoretical amino-hydrogen content is 13.16 equivalents/kg.

Silamine VII

This was made as for Silamine I but using 30.1 g of triethylchlorosilane. Silamine VII, i.e., bis(4-triethylsilylamino)phenyl)methane, has a theoretical amino-hydrogen equivalent weight of 106.5, i.e., its theoretical amino-hydrogen content is 9.38 equivalents/kg.

Silamine VIII

This was made as for Silamine IV but using 30.1 g of triethylchlorosilane. Silamine VIII, i.e., 1,1,3-trimethyl-3-(triethylsilylaminomethyl)-5-(triethylsilylamino)cyclohexane, has a theoretical amino-hydrogen equivalent weight of 99.5, i.e., its theoretical amino-hydrogen content is 10 equivalents/kg.

'Epoxide resin I' denotes a polyglycidyl ether of 2,2-bis(4-hydroxyphenyl)propane having a 1,2-epoxide content of 5.16 equivalents/kg and a viscosity at 21° C. of 24.5 Pa s.

'Epoxide resin II' denotes butane-1,4-diol diglycidyl ether having a 1,2-epoxide content of 9.0 equivalents/kg.

'Epoxide resin III' denotes N,N'-diglycidyl-5,5-dimethylhydantoin, having a 1,2-epoxide content of 8.3 equivalents/kg.

'Epoxide resin IV' denotes diglycidyl hexahydrophthalate, having a 1,2-epoxide content of 6.5 equivalents/kg.

EXAMPLE 1

Silamine I (24.0 g; 0.28 theoretical amino-hydrogen equivalent) and salicyclic acid (0.8 g) were mixed and placed in a glass container which was sealed with a polyethylene stopper. The mixture was perfectly stable on storage.

Into each of two glass containers was placed a mixture of Epoxide resin I (10 g; 0.052 epoxide equivalent), Epoxide resin II (10 g; 0.09 epoxide equivalent), Silamine I (12 g), and salicylic acid (0.4 g), and the containers were sealed as described above. The containers were stored for 3 months, at the end of which neither mixture showed any indication that any curing had taken place, remaining clear, mobile liquids throughout the storage period.

The stopper was then removed from one container so that the upper surface of the liquid came into contact with atmospheric moisture. The liquid solidified throughout its entire depth (40 mm) within 36 hours. The contents of the other, sealed container, however, remained a clear, mobile liquid.

EXAMPLE 2

Silamine II (6.6 g; 0.104 theoretical amino-hydrogen equivalent) and 2-methoxyethyl hydrogen maleate (0.4 g) were mixed and placed in a glass container and sealed as described in Example 1. The mixture remained a clear, mobile liquid.

In each of two such containers was placed a mixture of Silamine II (3.3 g), 2-methoxyethyl hydrogen maleate (0.2 g), and Epoxide Resin I (10 g; 0.052 epoxide equivalent). The containers were sealed and stored as described in Example 1. Both mixtures remained mobile liquids for over 3 months at room temperature, but when the stopper was removed from one container the contents solidified to a brittle solid throughout the entire depth (40 mm) within 24 hours while the contents in the sealed container remained unchanged.

EXAMPLE 3

Example 2 was repeated, except that dibutyl phthalate (3 g) was also incorporated into the epoxide resin-containing mixtures. These were stable in a sealed container for over 3 months but, once the stopper had been removed, the composition in the opened container cured to a hard solid within 48 hours.

EXAMPLE 4

Epoxide resin I (10 g; 0.052 epoxide equivalent), Silamine III (4 g; 0.027 theoretical amino-hydrogen equivalent), dibutyl phthalate (3 g), and salicylic acid (0.2 g) were mixed and placed in sealed glass containers as described in Example 1. The mixtures were stable in the containers for over 1 month but cured within 24 hours once the stopper had been removed.

EXAMPLE 5

Epoxide resin I (10 g; 0.052 epoxide equivalent), Epoxide resin II (10 g; 0.09 epoxide equivalent), Silamine IV (11.4 g; 0.146 theoretical amino-hydrogen equivalent), and salicylic acid (0.02 g) were mixed and placed in sealed glass containers as described in Example 1. The mixtures were stable in the containers but cured within 24 hours once the stopper had been removed.

EXAMPLE 6

Silamine II (9 g; 0.142 theoretical amino-hydrogen equivalent), Epoxide resin I (10 g; 0.052 epoxide equivalent), Epoxide resin II (10 g; 0.09 epoxide equivalent), and salicylic acid (0.3 g) were mixed and stored in a sealed container as described in Example 1. This mixture showed no signs of curing having taken place after 3 months' storage, but it cured completely within 48 hours once the stopper had been removed.

For purposes of comparison, this experiment was repeated, but omitting the salicylic acid. The mixture was perfectly stable on storage but did not cure rapidly once the stopper was removed, curing only slowly and taking about 2 weeks to cure completely. These experiments showed the accelerating effect that an acid has on the cure of the epoxide resin.

EXAMPLE 7

A composition as used in Example 6, containing salicylic acid, was placed in a glass tube to a depth of 30 mm and covered with an equal volume of water, which remained as a separate, upper layer. The lower (resin) layer solidified within 24 hours at room temperature.

EXAMPLE 8

A composition as used in Example 6, containing salicylic acid, was applied as a coating 20 μm thick to an aluminium sheet. This coating cured to a hard, glassy film within 24 hours at room temperature; it was unaffected when rubbed 20 times with a cotton wool swab soaked in acetone.

EXAMPLE 9

Epoxide resin I (10 g; 0.052 epoxide equivalent), Silamine II (3.3 g; 0.052 theoretical amino-hydrogen equivalent), and 2,6-di-tert.butyl-4-methyl phenol (3 g) were mixed and stored in a sealed container as described in Example 1. No evidence of curing having taken place in the mixture could be observed after 2 months at ambient temperature. When the stopper was removed this mixture cured to a hard solid within 4 days at ambient temperature.

EXAMPLE 10

Epoxide resin I (10 g; 0.052 epoxide equivalent), Silamine I (4.5 g; 0.052 theoretical amino-hydrogen equivalent), dibutyl phthalate (3 g), and an acid as specified below (0.2 g) were mixed and stored in sealed containers as described in Example 1. No evidence of curing having taken place could be observed after 1 month at ambient temperature. The time taken for the mixtures to cure once the stoppers had been removed, containing different acids, was as follows: acetic acid, 2½ days; 2,2-dichloropropionic acid, 1 day; methanesulphonic acid, 5 days; adipic acid, 3 days; cyanoacetic acid, 1 day; maleic acid, 2 days.

EXAMPLE 11

A mixture of Epoxide resin III (10 g; 0.083 epoxide equivalent), Silamine I (6 g; 0.07 theoretical amino-hydrogen equivalent), and 0.2 g of acetic acid was stable on storage at room temperature, whilst kept out of contact with atmospheric moisture, for at least 1 month. In the presence of water vapour a fresh sample of the mixture gelled in less than 24 hours.

EXAMPLE 12

A mixture of Epoxide resin IV (10 g; 0.065 epoxide equivalent), Silamine I (5 g; 0.058 theoretical amino-hydrogen equivalent), and 0.2 g of acetic acid was stable on storage at room temperature for at least 1 month while ingress of atmospheric moisture was prevented. In the presence of water vapour a fresh sample of the mixture had cured in 4 days.

EXAMPLE 13

A mixture of Epoxide resin I (10 g; 0.052 epoxide equivalent), Epoxide resin II (10 g; 0.09 epoxide equivalent), Silamine V (11 g; 0.157 theoretical amino-hydrogen equivalent), and 0.4 g of salicylic acid was stable for 17 days but a fresh sample, with access to atmospheric moisture, cured within 2 days.

EXAMPLE 14

The process of Example 12 was repeated except that there was used 11 g (0.145 theoretical amino-hydrogen equivalent) of Silamine VI. Whereas the mixture protected from atmospheric moisture showed signs of gelling only after 6 days, another sample cured within 2 days in the presence of water vapour.

EXAMPLE 15

A mixture of Epoxide resin I (20 g; 0.104 epoxide equivalent), Silamine VII (11.2 g; 0.105 theoretical amino-hydrogen equivalent), dibutyl phthalate (6 g), and salicylic acid (0.4 g) was stable in the absence of atmospheric moisture for at least one month but gelled within 5 days when exposed to atmospheric moisture.

EXAMPLE 16

The procedure of Example 14 was repeated, using Silamine VIII (11 g; 0.11 theoretical amino-hydrogen equivalent) in place of Silamine VII and 20 g of dibutyl phthalate. While the mixture, sealed from atmospheric moisture, was stable for at least a month, a sample exposed to such moisture gelled within 5 days.

What is claimed is:
1. Compositions for curing epoxide resins and activated by water, said compositions comprising
(a) a silamine of the formula

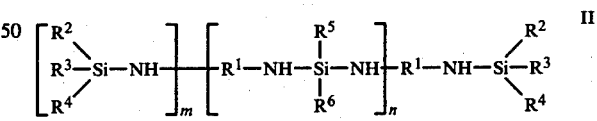

where
either m represents 1, in which case $R^1$ represents the divalent residue of an aromatic, aliphatic, araliphatic, or cycloaliphatic diprimary amine after removal of the two primary amino groups and n represents zero or an integer of from 1 to 10, or m represents 2, in which case $R^1$ represents the trivalent residue of an aliphatic triprimary amine after removal of the three primary amino groups and n represents zero, and
$R^2$, $R^3$, $R^4$, $R^5$, and $R^6$, which may be the same or different, each represent an alkyl group of 1 to 8 carbon atoms or an aryl group of 6 to 10 carbon atoms, and (b) as accelerator, a substantially anhydrous organic acid or a substantially anhydrous phenol.

2. The compositions of claim 1, wherein $R^1$ represents a group having from 2 to 20 carbon atoms.

3. The compositions of claim 1, wherein $R^1$ represents an ethylene, hexamethylene, trimethylhexamethylene, xylylene, cyclohexylene, substituted cyclohexylene of formula

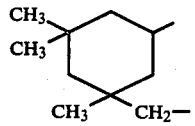 III bis(phenylene)methane, bis(phenylene) sulfone, 2,2-bis(phenylene)-propane, or phenylene group.

4. The compositions of claim 1 in which $R^2$, $R^3$, $R^4$, $R^5$, and $R^6$ each represent methyl, ethyl, n-propyl, phenyl, or phenyl substituted by one or more alkyl groups of 1 to 4 carbon atoms or by one or more halogen atoms.

5. The compositions of claim 1 in which component (b) is acetic, phthalic, methanesulfonic, salicylic, maleic, 2,2-dichloropropionic, adipic, trimellitic, or cyanoacetic acid or, where such acid is di- or polybasic, a partial ester of the acid.

6. The compositions of claim 1 in which component (b) is phenol itself, an alkylated phenol, a halogenated phenol, resorcinol, bisphenol F, or bisphenol A.

7. The compositions of claim 1 which further contain (c) an epoxide resin.

8. The compositions of claim 7 in which the weight ratio of the said acid or phenol to the epoxide resin is within the range 0.5–20:100.

9. The compositions of claim 7 which contain sufficient of the silamine to supply from 0.7 to 1.4 aminohydrogen equivalents, calculated after removal of substantially all the silyl groups, per 1,2-epoxide equivalent of the epoxide resin.

10. A process for curing an epoxide resin which comprises exposing the compositions of claim 7 to liquid water or water vapour at ambient or elevated temperature.